(12) United States Patent
Jinno et al.

(10) Patent No.: US 7,261,726 B2
(45) Date of Patent: *Aug. 28, 2007

(54) MEDICAL MANIPULATOR

(75) Inventors: Makoto Jinno, Tokyo (JP); Takamitsu Sunaoshi, Kanagawa-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/289,334

(22) Filed: Nov. 30, 2005

(65) Prior Publication Data

US 2006/0079866 A1 Apr. 13, 2006

Related U.S. Application Data

(63) Continuation of application No. 10/661,636, filed on Sep. 15, 2003, now Pat. No. 6,994,716.

(30) Foreign Application Priority Data

Sep. 18, 2002 (JP) .............................. 2002-271947

(51) Int. Cl.
*A61B 17/32* (2006.01)
(52) U.S. Cl. ....................... 606/170; 606/205; 600/131; 700/245; 414/2
(58) Field of Classification Search ............... 606/1, 606/139, 170, 205–211; 600/102, 130, 131; 700/245, 260, 261; 414/1–5
See application file for complete search history.

(56) References Cited

U.S. PATENT DOCUMENTS

| 5,021,969 | A | 6/1991 | Okamura et al. |
| 6,853,879 | B2 | 2/2005 | Sunaoshi |
| 6,889,116 | B2 | 5/2005 | Jinno |
| 6,994,716 | B2 * | 2/2006 | Jinno et al. ................ 606/170 |
| 2006/0074408 | A1 * | 4/2006 | Jinno et al. .................... 606/1 |
| 2006/0079865 | A1 * | 4/2006 | Jinno et al. .................... 606/1 |

FOREIGN PATENT DOCUMENTS

| JP | 7-328024 | 12/1995 |
| JP | 2000-350735 | 12/2000 |
| JP | 2001-277157 | 10/2001 |

* cited by examiner

*Primary Examiner*—A. Farah
(74) *Attorney, Agent, or Firm*—Oblon, Spivak, McClelland, Maier & Neustadt, P.C.

(57) ABSTRACT

A medical manipulator comprises a working unit (10) that performs operations, an operating unit (20) that generates instructions, a drive unit (50) that drives the working unit on the basis of instructions given thereto by the operating unit, a power transmission mechanism (60) for transmitting driving force of the drive unit to the working unit, and a control unit (40) for controlling the power transmission mechanism on the basis of instructions given thereto by the operating unit. The power transmission mechanism includes a first power transmission unit (61) interlocked with the drive unit, and a second power transmission unit (63) interlocked with the working unit and capable of being detachably connected to the first power transmission unit. A back drive torque of the first power transmission unit is larger than a back drive torque of the second power transmission unit.

6 Claims, 10 Drawing Sheets

MEDICAL MANIPULATOR

CROSS-REFERENCE TO RELATED APPLICATIONS

This application is a continuation of U.S. patent application Ser. No. 10/661,636, filed on Sep. 15, 2003, now U.S. Pat. No. 6,994,716. This application is further based upon and claims the benefit of priority from the prior Japanese Patent Application No. 2002-271947, filed on Sept. 18, 2002; the entire contents of which are incorporated herein by reference.

BACKGROUND OF THE INVENTION

1. Field of the Invention

The present invention relates to a medical manipulator and, more particularly, to a medical manipulator having a simple mechanism and excellent in operability and safety.

2. Description of the Related Art

Referring to FIG. 13, laparoscopic cholecystectomy forms three small incisions 151, 152 and 153 in the abdominal wall, fits tracheal tubes 154 in the incisions 151, 152 and 153, inserts an endoscope 161, and forceps 171 and 172 through the tracheal tubes 154 into the abdomen. An operator 160, usually, a surgeon, conducts an operation, watching an image taken by the endoscope 161 and displayed on the screen of a monitor 162. Laparoscopic cholecystectomy reduces physical load on the subject and reduces the number of days for which the convalescent patient is obliged to stay in the hospital before leaving the hospital because laparoscopic cholecystectomy does not need to incise the abdominal wall. The field to which such a surgical operation is applicable is expected to expand.

Studies have been made for the development of techniques relating to remote-controlled robots, such as master-slave manipulators, to be applied to the medical field, and some techniques have been applied to clinical purposes (http://www.computermotion.com, http://www.intuitivesurgical.com). Techniques relating to remote-controlled robots provide a master-slave manipulator system including a master arm to be operated by an operator, and a slave arm for actually treating a diseased part, completely separated from the master arm. Electric signals corresponding to instructions given by operating the master arm are transmitted to the slave arm. Usually, the master arm and the slave arm are articulated arms having at least six degrees of freedom of motion. The master-slave manipulator system is a complicated system including a controller for controlling the joints of the articulated arms, an electrical control system, and many parts including wiring lines.

The inventors of the present invention proposed previously a simple medical manipulator (robotic forceps) developed by applying robot techniques to a conventional pair of forceps as shown in FIG. 14 in JP2000-350735A (Patent document 1). Referring to FIG. 14, this previously proposed medical manipulator comprises a control unit 20 including a position controller 23 and an operation controller 24, a connecting unit 30 having one end connected to control unit 20, a working unit 10 connected to the other end of the connecting unit 30 and including support devices 15 and 16 supporting an end effector having operating members 14 for motions with at least two degrees of freedom, and a controller, not shown, for changing the positions of the operating members 14 of the end effector by controlling the support devices 15 and 16 according to instructions given by the position controller 23 and operating the operating members 14 of the end effector according to instructions given by the operation controller 24.

The inventors of the present invention proposed previously a medical manipulator as shown in FIG. 15 having degrees of freedom of motion suitable for suture and ligation in JP2002-102248A (Patent document 2). This medical manipulator comprises a working unit 10, a control unit 20, and a connecting unit 30 having opposite ends respectively connected to the working unit 10 and the control unit 20. The working unit 10 includes a support device capable of turning about a first axis 11 perpendicular to the axis 31 of the connecting unit 30, and a second axis perpendicular to the first axis 11, and an end effector for treating a diseased part. The end effector has a gripper 14 is capable of turning about an axis substantially parallel to the second axis 12. The working unit 10 has a pitching joint 15 and a rolling joint 16 for moving the gripper 14 with two degrees of freedom. The control unit 20 includes a position controller 23 capable of turning about a third axis 21 perpendicular to the axis 31 of the connecting unit 30 and a fourth axis 22 perpendicular to the third axis 21, and an operation controller 24 to be operated by an operator. The operator grips the operation controller 24. The wrist of the operator gripping the operation controller 24 turns about an axis substantially parallel to the fourth axis 22. The gripping motion of the gripper 14 for treating a diseased part is controlled by operating the operation controller 24.

This previously proposed medical manipulator, differing from the remote-controlled master-slave manipulator, is formed by connecting the control unit (master unit) and the working unit, i.e., hand or forceps (slave unit) by the connecting unit, and is capable of achieving both simple, reliable, quick, large operations that can be performed by the operator, which is an advantage of the conventional forceps, and delicate, difficult operations and operations from difficult directions, which is an advantage of the manipulator. Since the working unit is provided with joints for bending and turning motions, the position of the end effector can freely be adjusted. Therefore, suturing and ligating operations from various directions, which have been difficult for the conventional forceps to perform, can easily be performed. The operator is able to use the medical manipulator and the conventional forceps simultaneously by operating the medical manipulator by the right hand and operating the forceps by the left hand. The simple, compact medical manipulator is inexpensive.

Medical instruments, particularly, surgical instruments, as well as medical robots, cannot be used for surgical operations unless those instruments are sterilized and cleaned. Generally, the working parts of medical robots, medical devices and surgical instruments are smeared with the blood and tissues of subjects of operations, and hence need to be washed clean and to be sterilized. At least the working unit, that comes into contact with the subject, of a large device can be removed from the main unit or can be separated from the control unit for cleaning and sterilization. Therefore, it is essential that the working units of medical robots, medical devices and surgical instruments are separable from the control units. The working unit separated for sterilization from the control unit must be capable of being combined with the control unit at a predetermined position relative to the control unit and in a predetermined orientation relative to the control unit.

Generally, a robot must be capable of a resetting operation, i.e., an initializing operation, when the robot is connected to a power source. The initializing operation operates the joints of the robot according to a predetermined sequential procedure to detect the arrival of the joints at their initial positions by initialization sensors incorporated into the joints, sets the joints in initial angular positions, and resets incremental encoders respectively combined with the output shafts of motors. It is very troublesome to operate a medical robot for initialization for returning the medical robot to its initial positional state during a surgical operation. Thus, it is desired that such an initializing operation is avoided as far as possible in a tense situation of a surgical operation. Therefore, it has been desired to develop a medical robot that can immediately be used after the same has been connected to a power source without requiring any initializing operation.

The medical manipulator previously proposed by the inventors of the present invention is provided integrally with the master unit and the slave unit, the operator who operates the medical manipulator must bear the weight of the medical manipulator. Therefore, it is the most important problem to form the medical manipulator in a small, lightweight structure. Therefore, it is very difficult, in respect of available spaces and allowable weight, to combine initialization sensors with the joints and other necessary parts. Even if initialization sensors could be combined with the joints and other necessary parts, a large number of wiring lines are necessary for connecting the initialization sensors to the associated parts and devices, which increases the weight of the medical manipulator and deteriorates the operability of the medical manipulator significantly.

Although a robot capable of always securing an absolute position without performing an initializing operation can be formed by providing the robot with absolute encoders, the absolute encoders are larger and need more wiring lines than incremental encoders. Thus, the employment of absolute encoders is not suitable for the medical manipulator previously proposed by the inventors of the present invention.

SUMMARY OF THE INVENTION

Accordingly, it is an object of the present invention to solve the foregoing problems in the prior art and to provide a small, lightweight, medical manipulator, excellent in operability, not requiring any initializing operation before starting a surgical operation, and including a working unit capable of being connected to and disconnected from a drive unit for cleaning and sterilization, and capable of being interlocked with the drive unit.

According to the present invention, a medical manipulator comprises: a working unit that performs operations; an operating unit that generates instructions; a drive unit that drives the working unit on the basis of instructions given thereto by the operating unit; a power transmission mechanism for transmitting driving force of the drive unit to the working unit; and a control unit for controlling the power transmission mechanism on the basis of instructions given thereto by the operating unit; wherein the power transmission mechanism includes a first power transmission unit interlocked with the drive unit, and a second power transmission unit interlocked with the working unit and capable of being detachably connected to the first power transmission unit, and a back drive torque of the first power transmission unit is larger than a back drive torque of the second power transmission unit.

In the medical manipulator according to the present invention, the control unit is capable of executing operations specified by a control program for setting the first power transmission unit in a predetermined initial positional state at the normal completion of an operation.

In the medical manipulator according to the present invention, the control program waits in a waiting state where the control unit is initialized by connecting the medical manipulator to a power source for an operation start instruction specifying an operation for setting the operating unit in an operational state, a return-to-origin instruction specifying an operation for setting the first power transmission unit in the predetermined initial positional state or a shutdown instruction specifying an operation for disconnecting the medical manipulator from the power source, and the control program makes the shutdown instruction effective only when it is confirmed that the first power transmission unit has been set in the predetermined initial positional state.

The medical manipulator according to the present invention may further comprise an initialization detecting means capable of being connected to the first power transmission unit when the first power transmission unit is disconnected from the second power transmission unit and of detecting components of the first power transmission unit set at predetermined joining positions, respectively.

In the medical manipulator according to the present invention, the back drive torque of the first power transmission unit has a strength more than 0.05 N·m when the first and the second power transmission unit are connected together.

In the medical manipulator according to the present invention, the working unit and the second power transmission unit are integrated in an assembly, the operating unit and the first power transmission unit are integrated in an assembly, and the assembly of the working unit and the second power transmission unit, and the assembly of the operating unit and the first power transmission unit can detachably connected together.

In the medical manipulator according to the present invention, the working unit and the second power transmission unit are integrated in an assembly; and the assembly of the working unit and the second power transmission unit, the first power transmission unit, and the operating unit can detachably be connected together.

Since the first power transmission unit and the second power transmission unit can detachably be connected, and a back drive torque of the first power transmission unit is larger than a back drive torque of the second power transmission unit, the working unit can be cleaned and sterilized, a return-to-origin operation can be carried out without using any absolute encoders or origin sensors, and the working unit can always be set in its initial state before and after connecting the working unit to and disconnecting the same from the drive unit.

Since the control unit sets the first power transmission unit in the predetermined initial positional state after the normal completion of an operation, the medical manipulator can be used immediately after the connection of the same to the power source without requiring a troublesome return-to-origin operation. Thus, troublesome work in a tense situation of surgical operation can be avoided and thereby the efficiency of the surgical operation can remarkably be improved.

Since the initialization detecting means is capable of being detachably connected to the first power transmission unit, the initialization of the drive unit can be detected without permanently mounting the initialization detecting means on the first power transmission unit, and the return-to-origin operation is possible even in a state where the operation is ended abnormally.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
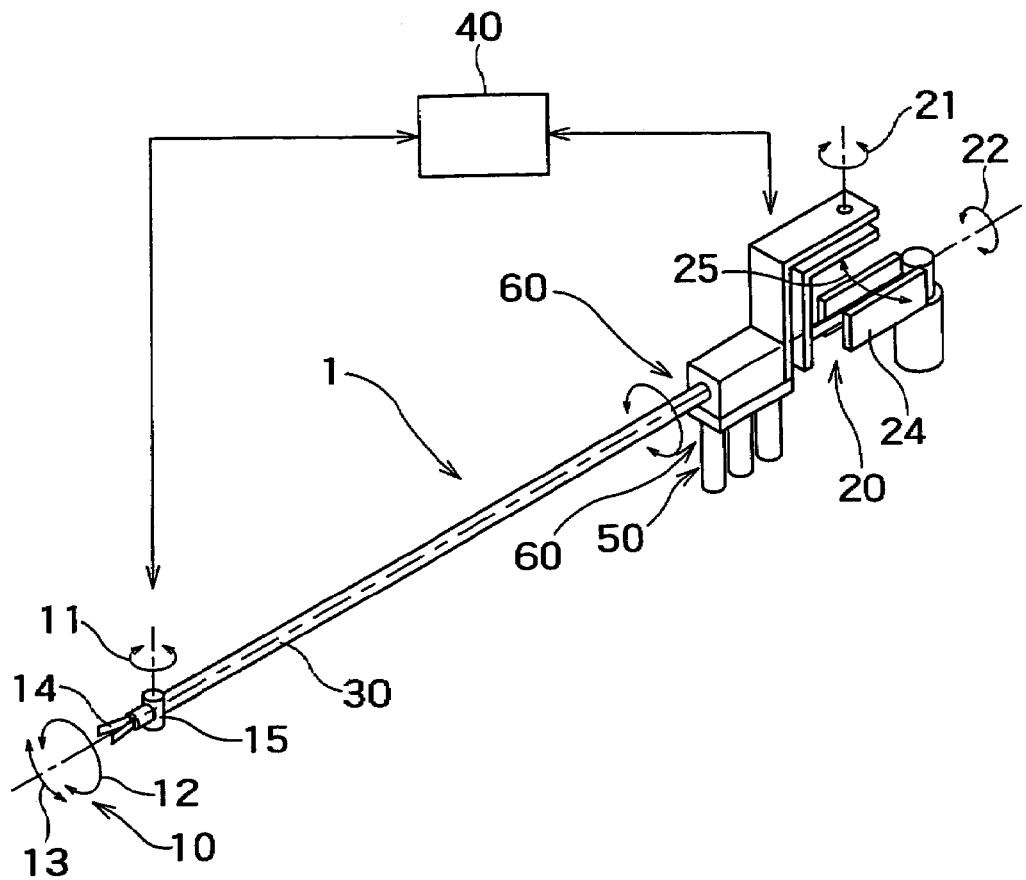
FIG. 1 is a schematic perspective view of a medical manipulator in a first embodiment according to the present invention.

Referring to FIG. 1, a medical manipulator 1 in a first embodiment according to the present invention comprises a working unit 10 that performs necessary operations, an operating unit 20 for generating instructions specifying operations to be performed by the working unit 10, a drive unit 50 for driving the working unit 10 on the basis of instructions generated by the operating unit 20, a power transmission mechanism 60 for transmitting the drive force of the drive unit 50 to the working unit 10, and a control unit 40 for controlling the power transmission mechanism 50 to make the working unit 10 operate on the basis of instructions generated by the operating unit 20. The working unit 10 and the operating unit 20 are connected by a bar-shaped connecting unit 30. The working unit 10 is disposed at one end of the connecting unit 30, and the operating unit 20 and the drive unit 50 are disposed near the other end of the connecting unit 30. The drive unit 50 includes three motors. The number of degrees of freedom of motion and the arrangement of joints do not need to be limited to those shown in FIG. 1.

The power transmission mechanism 60 is interlocked through the connecting unit 30 with the working unit 10, and is interlocked with the drive unit 50. The power transmission mechanism 60 includes a first power transmission unit 61 interlocked with the drive unit 50, and a second power transmission unit 63 interlocked with the working unit 10. The first power transmission unit 61 and the second power transmission unit 63 are engaged detachably to connect the working unit 10 and the driving unit 50 separably. The power transmission mechanism 60 includes a plurality of power transmitting elements including, for example, links, gears, a wire-pulley mechanism, a reduction gear and couplings. The power transmission mechanism 60 transmits the driving power of the drive unit 50 including the motors to the working unit 10 by the wire-pulley mechanism disposed in the connecting unit 30 to drive the working unit 10 for operations including bending operations, turning operations, gripping operations.

Figure 2:
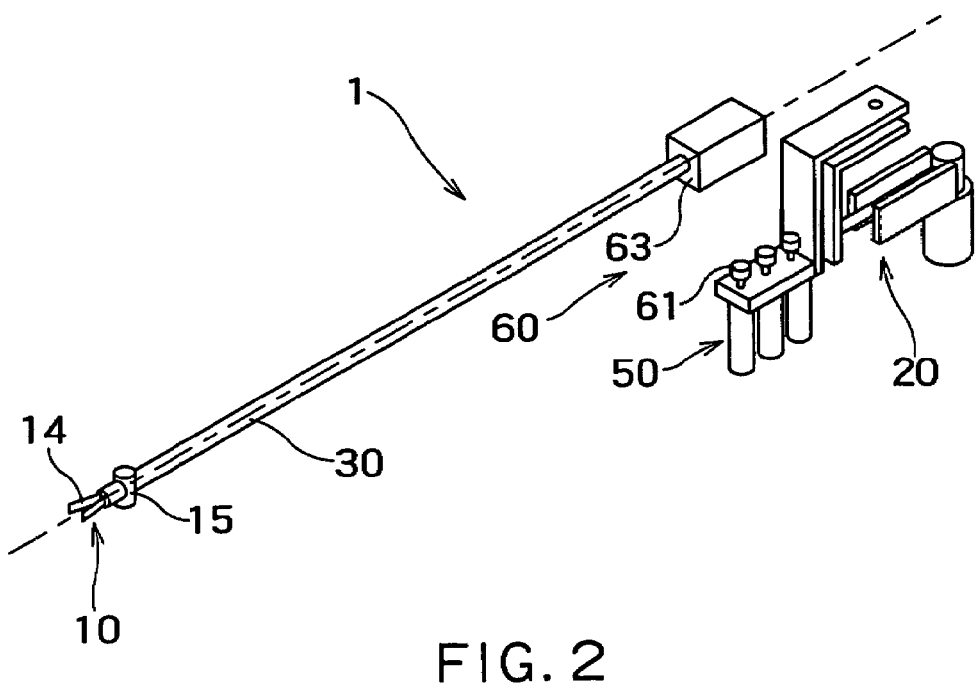
FIG. 2 is a perspective view of the medical manipulator shown in FIG. 1 as divided by a first dividing method.
Figure 3:
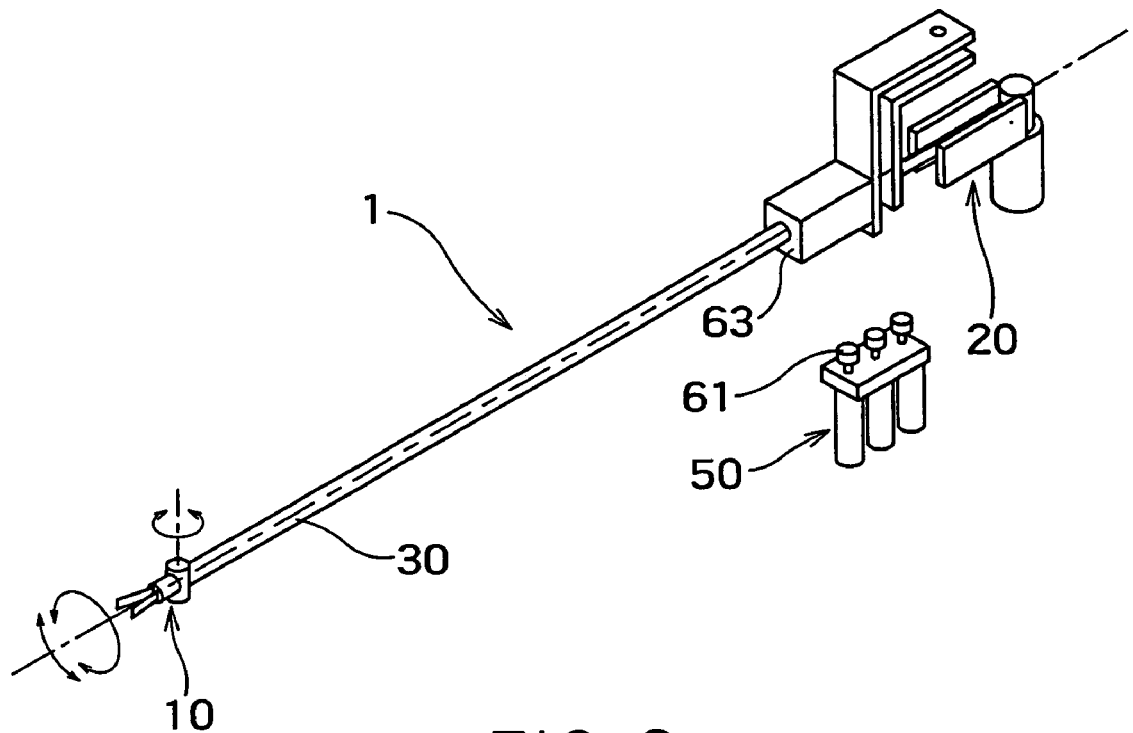
FIG. 3 is a perspective view of the medical manipulator shown in FIG. 1 as divided by a second dividing method.
Figure 4:
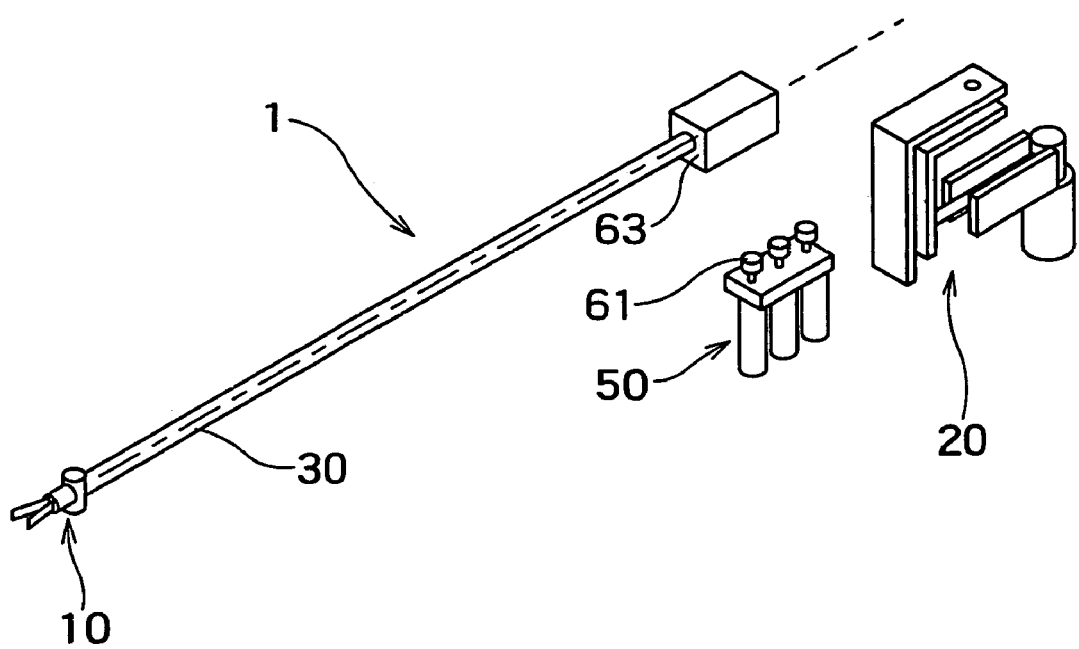
FIG. 4 is a perspective view of the medical manipulator shown in FIG. 1 as divided by a third dividing method.

FIG. 2 shows the medical manipulator 1 divided into an assembly of the working unit 10 and the connecting unit 30 and that of the operating unit 20 and the drive unit 50. The medical manipulator 1 may be divided into an assembly of the working unit 10, the connecting unit 30 and the operating unit 20, and the drive unit 50 as shown in FIG. 3, may be divided into an assembly of the working unit 10 and the connecting unit 30, the operating unit 20 and the drive unit 50 as shown in FIG. 4. The medical manipulator 1 will be described on an assumption that working unit 10 and the drive unit 50 are connected separably as shown in FIG. 2.

Figure 7:
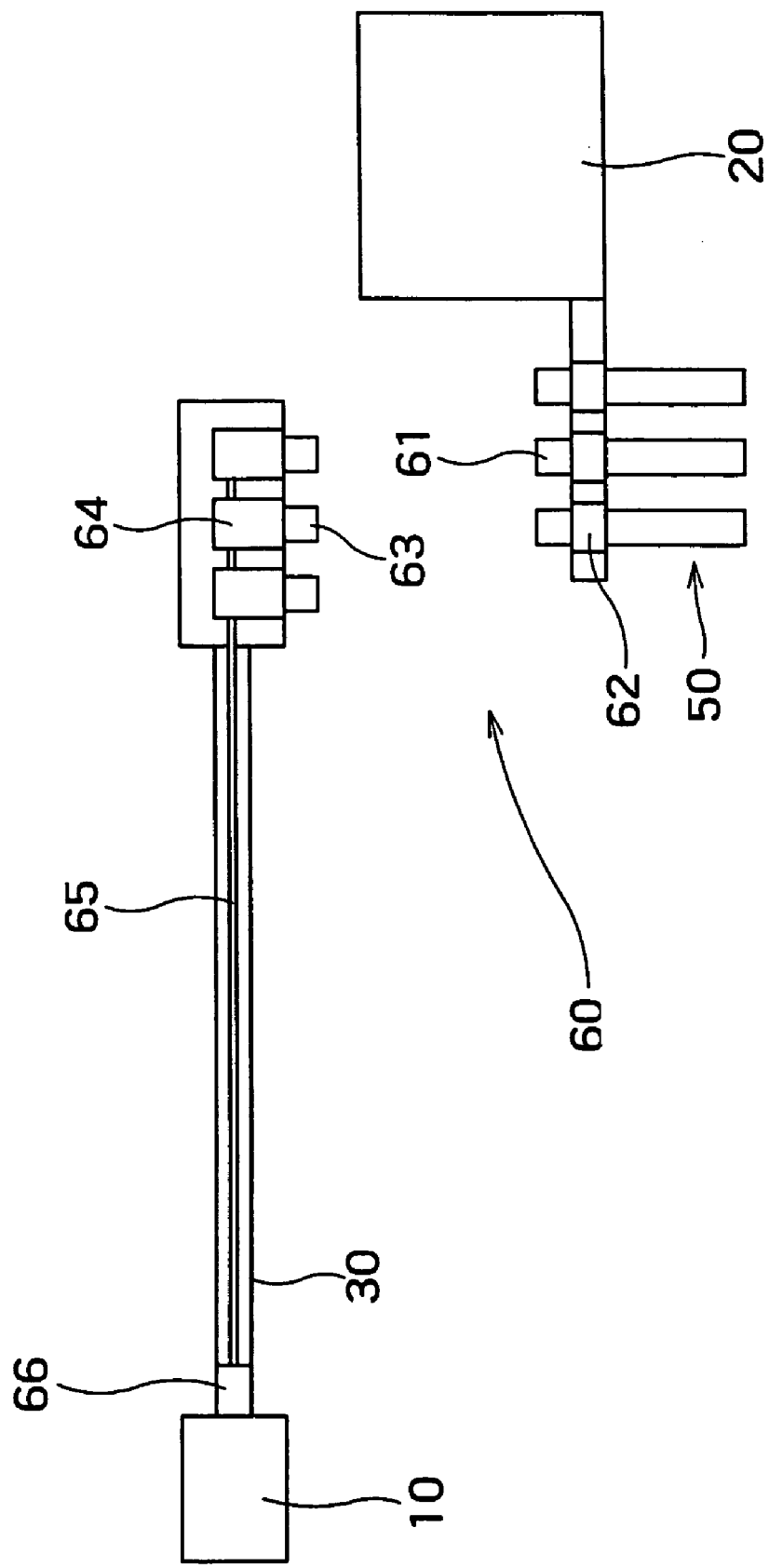
FIG. 7 is a side elevation of the medical manipulator of assistance in explaining a power transmission mechanism.

Referring to FIGS. 2 and 7, the power transmission mechanism 60 has a first power transmission unit 61 including couplings and interlocked with the drive unit 50, a power transmitting device 62 including reduction gears and interposed between the first power transmission unit 61 and the drive unit 50; a second power transmission unit 63 including couplings and interlocked with the working unit 10; a power transmitting device 64 including pulleys connected to the second power transmission unit 63; a power transmitting device 65 including a wire rope or a rod connected to the power transmitting device 64; and a power transmitting device 66 interlocking the power transmitting device 65 and the working unit 10 and including pulleys, gears and links. Power can be transmitted from the drive unit 50 to the working unit 10 by connecting the first power transmission unit 61 including the couplings, and the second power transmission unit 63 including the couplings. The power transmission mechanism 60 may be any other suitable combination of power transmitting devices.

Figure 8:
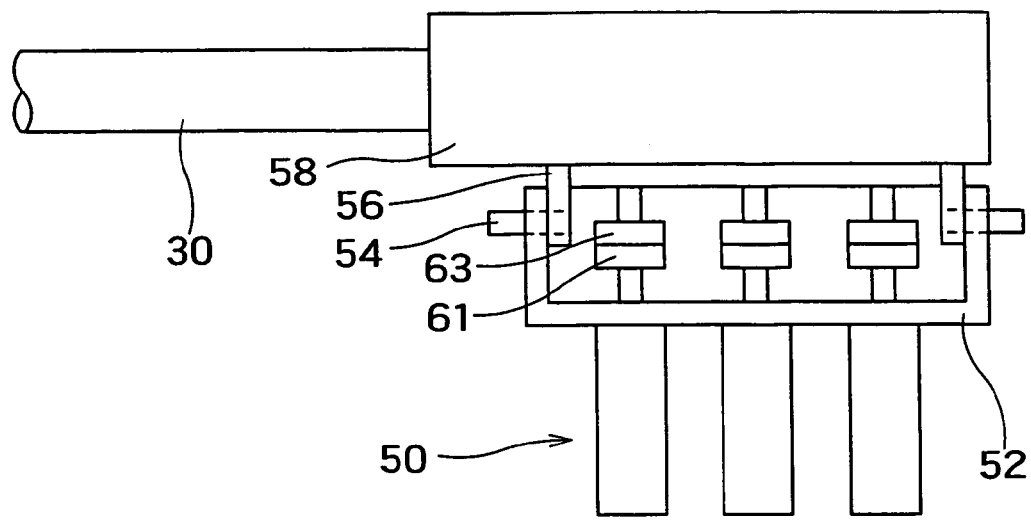
FIG. 8 is a view of assistance in explaining operations for connecting and disconnecting a working unit and a drive unit included in the medical manipulator shown in FIG. 1.
Figure 9:
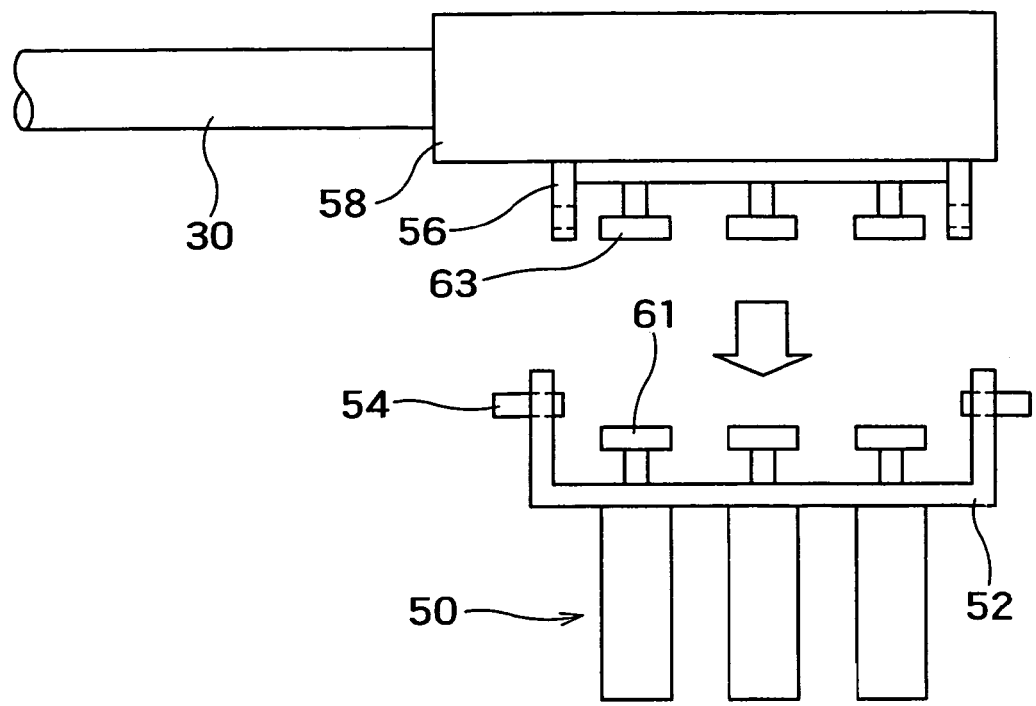
FIG. 9 is a view of assistance in explaining operations for connecting and disconnecting the working unit and the drive unit included in the medical manipulator shown in FIG. 1.

FIG. 8 and FIG. 9 are views of assistance in explaining operations for connecting and disconnecting the working unit 10 and the drive unit 50 of the manipulator 1. The drive unit 50 including three drive motors, and the first power transmission unit 61 are mounted on a base 52. The second power transmission unit 63 and a housing 58 are mounted on a base 56. The housing 58 is connected to an end part of the connecting unit 30. The power transmitting device 64 is contained in the housing 58. Latching pins 54 connect the bases 52 and 56 separably. The base 52 is separated from the base 56 to separate the first power transmission unit 61 from the second power transmission unit 63. In connecting the first power transmission unit 61 and the second power transmission unit 63, the first power transmission unit 61 and the second power transmission unit 63 are set opposite to each other. Then, the first power transmission unit 61 adjusts the position of the second power transmission unit 63 so that the first power transmission unit 61 and the and the second power transmission unit 63 are connected in the same positional relationship as a predetermined positional relationship in which the first power transmission unit 61 and the second power transmission unit 63 had been connected before the same were separated from each other. After the first power transmission unit 61 and the second power transmission unit 63 have been set in the predetermined positional, the bases 52 and 56 are fastened together by the latch pins 54. Thus, the medical manipulator 1 can securely set in the initial state. The first power transmission unit 61 and the second power transmission unit 63 may be connected and separated by using any suitable fastening means such as screws, instead of using the bases 52 and 56 and the latch pins 54.

The first power transmission unit 61 and the second power transmission unit 63 are disconnected after the completion of an operation, such as a surgical operation, to clean and sterilize the working unit 10. A connecting procedure for connecting the first power transmission unit 61 and the second power transmission unit 63 after the working unit 10 has been cleaned and sterilized will be described. The first power transmission unit 61 is capable of exerting a back drive torque sufficient for holding the couplings of the first power transmission unit 61 at positions at which the couplings are located before the first power transmission unit 61 and the second power transmission unit 63 are disconnected after the first power transmission unit 61 and the second power transmission unit 63 have been disconnected. The back drive torque is a torque necessary for transmitting power from the first power transmission unit 61 to the drive unit 50. The sufficient back drive torque of the first power transmission unit 61 restrains the couplings of the first power transmission unit 61 from being moved manually for positional change.

When the operation of the medical manipulator 1 is completed normally, the control unit 40 sets the first power transmission unit 61 in its initial positional state. Therefore, the first power transmission unit 61 is in its initial positional state when the working unit 10 is separated from the drive unit 50 after the operation of the medical manipulator 1 has normally been completed. Since the first power transmission unit 61 has a sufficient back drive torque, the first power transmission unit 61 remains in the initial positional state until the first power transmission unit 61 and the second power transmission unit 63 are connected again. Since the back drive torque of the first power transmission unit 61 has a strength more than 0.05 N·m, the first power transmission unit 61 cannot rotate as long as the drive torque more than 0.05 N·m is not applied to the outside diameter portion of the first power transmission unit 61. Thus, the first power transmission unit 61 has the sufficient back drive torque so that the first power transmission unit 61 restrains the couplings of the first power transmission unit 61 from being moved manually for positional change.

When the second power transmission unit 63 interlocked with the working unit 10 is disconnected from the first power transmission unit 61, the couplings of the second power transmission unit 63 can manually be moved by a relatively low torque. Therefore, the couplings of the second power transmission unit 63 are not necessarily held, after the working unit 10 has been cleaned and sterilized, at positions where the couplings of the second power transmission unit 63 were positioned when the second power transmission unit 63 was disconnected from the first power transmission unit 61, and it is highly possible that the positions of the couplings of the second power transmission unit 63 are changed. If the positions of the couplings of the second power transmission unit 63 are changed after the second power transmission unit 63 has been disconnected from the first power transmission unit 61, the first power transmission unit 61 and the second power transmission unit 63 cannot be connected in the same positional relationship as before. The first power transmission unit 61 is capable of exerting the sufficiently high back drive torque and the couplings of the second power transmission unit 63 can be turned by a relatively low torque. Thus, since a back drive torque of the first power transmission unit 61 is larger than a back drive torque of the second power transmission unit 63, the couplings of the second power transmission unit 63 can be turned, when the second power transmission unit 63 is brought into engagement with the first power transmission unit 61, by the first power transmission unit 61 to the positions where the couplings of the second power transmission unit 63 were positioned and were aligned with the corresponding couplings of the first power transmission unit 61 when the second power transmission unit 63 was disconnected from the first power transmission unit 61.

Since the working unit 10 touches the subject's body directly and is smeared with blood and tissues, the working unit 10 used for a surgical operation needs to be disconnected from the drive unit 50 and to be cleaned and sterilized. In cleaning the working unit 10, the components of the second power transmission unit 63 and the power transmitting devices 64, 65 and 66 must manually be moved to wash off blood and tissues remaining in gaps in the components of the second power transmission unit 63 and the power transmitting devices 64, 65 and 66. Therefore, it is usual for the positions of the couplings of the second power transmission unit 63 to change from those where the couplings were positioned when the second power transmission unit 63 was disconnected from the first power transmission unit 61. Since the couplings of the second power transmission unit 63 can be moved, as mentioned above, to the positions where the couplings of the second power transmission unit 63 can be joined to those of the first power transmission unit 61 held at the initial positions after the disconnection of the second power transmission unit 63 from the first power transmission unit 61, the first power transmission unit 61 and the second power transmission unit 63 can be connected in the predetermined positional relationship.

Thus, the medical manipulator 1 of the present invention can easily be restored to its initial state after disconnecting the working unit 10 from the drive unit 50 and cleaning and sterilizing the working unit 10, even if the positional state of the second power transmission unit 63 is changed after disconnecting the second power transmission unit 63 from the first power transmission unit 61. The medical manipulator 1 may be subjected to a sterilizing process after the same has been cleaned and reassembled.

Thus, the working unit 10 can be set in the predetermined positional state in connecting the second power transmission unit 63 to the first power transmission unit 61 after disconnecting the working unit 10 from the drive unit 50 without using any absolute encoders and origin sensors. Thus, the medical manipulator can be formed in a small, lightweight structure and is excellent in operability.

Figure 5:
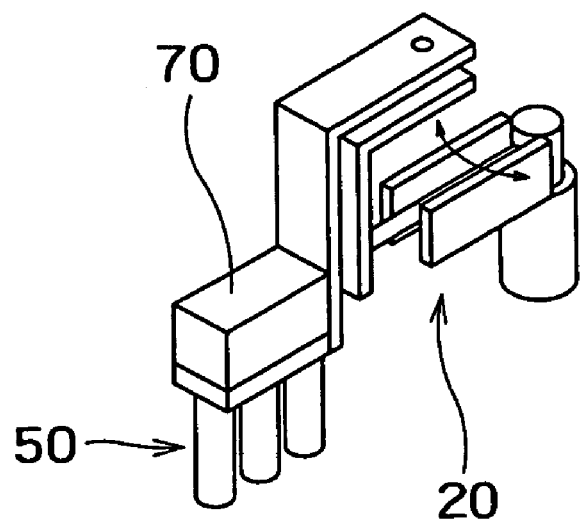
FIG. 5 is a perspective view of an operating unit included in a medical manipulator in a second embodiment according to the present invention provided with an initialization detecting device.
Figure 6:
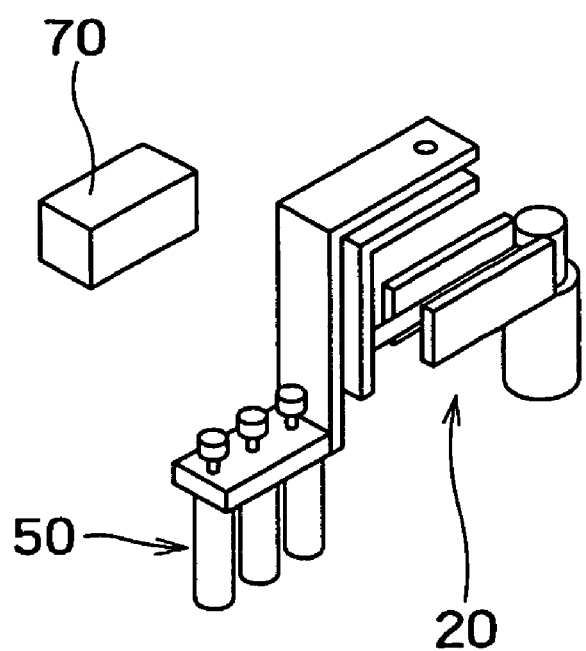
FIG. 6 is an exploded perspective view of the operating unit shown in FIG. 5.

A medical manipulator 1 in a second embodiment according to the present invention will be described with reference to FIGS. 5, 6, 10 and 11. The medical manipulator 1 has a first power transmission unit 61 and a second power transmission unit 63. As shown in FIGS. 5 and 6, an initialization detector 70 can be combined with the first power transmission unit 61. The initialization detector 70 can freely be combined with and separated from the first power transmission unit 61 after the first power transmission unit 61 has been disconnected from the second power transmission unit 63. The initialization detector 70 is combined with the first power transmission unit 61 after disconnecting the first power transmission unit 61 from the second power transmission unit 63.

Figure 10:
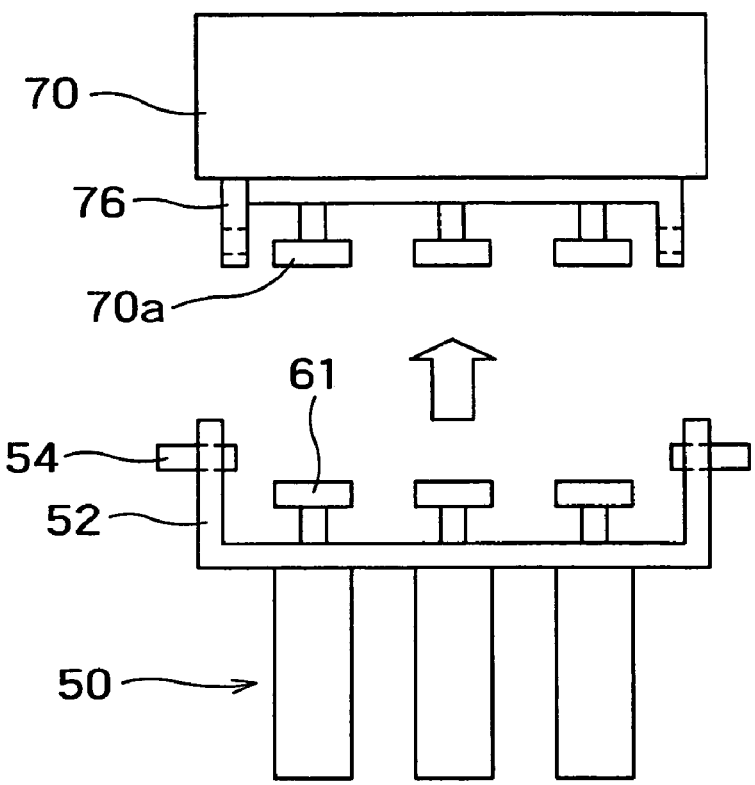
FIG. 10 is a view of assistance in explaining operations for connecting and disconnecting the drive unit.
Figure 11:
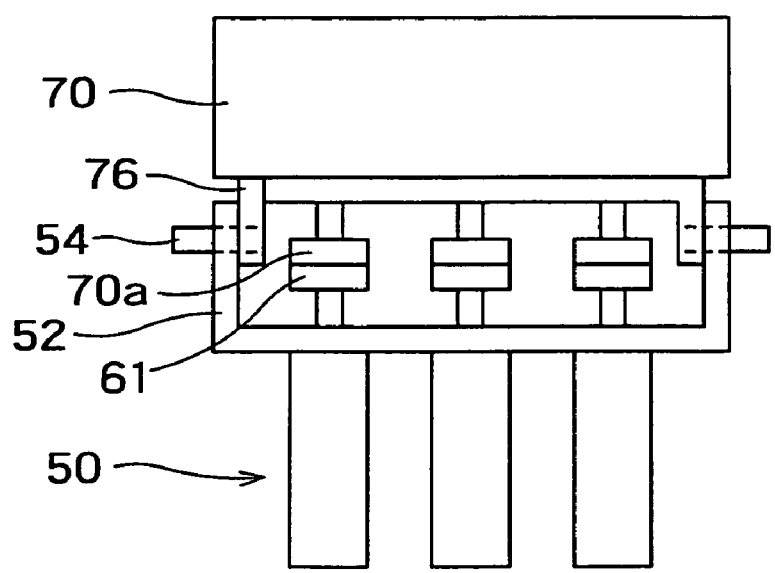
FIG. 11 is a side elevation of an initialization detector included in the medical manipulator of the present invention.

Referring to FIGS. 10 and 11, the initialization detector 70 is mounted on a base 76. The initialization detector 70 has couplings 70a supported on the base 76. The couplings 70a are engaged with the couplings of the first power transmission unit 61, and then the base 76 is fastened to a base 52 holding the first power transmission unit 61 by latch pins 54. Subsequently, the motors of a drive unit 50 are actuated to set the first power transmission unit 61 in its initial positional state. The initialization of the first power transmission unit 61, i.e., the completion of setting the first power transmission unit 61 in the initial positional state, is detected by the initialization detector 70. After the first power transmission unit 61 has thus been set in the initial positional state, the initialization detector 70 is removed from the first power transmission unit 61, and then the second power transmission unit 63 is connected to the first power transmission unit 61 to interlock a working unit 10 with the drive unit 50.

The initialization detector 70, which is capable of being detachably connected to the first power transmission unit 61, does not need to be kept connected to the first power transmission unit 61. Thus, the first power transmission unit 63 can be set in the initial positional state even if the operation of the medical manipulator 1 is stopped abnormally and the first power transmission unit 61 interlocked with the drive unit 50 is not stopped in the initial positional state. Therefore, the medical manipulator 1 can be restored to its initial state even if the same is stopped abnormally, for example, in an emergency. The medical manipulator 1 does not need any origin sensor, can be formed in a small, light weight structure and is excellent in operability. The medical manipulator is safe because the initialization detector 70 can be connected to and disconnected from the first power transmission unit 61 even in an emergency during a surgical operation without causing harm to the subject.

A manipulator stopping procedure for normally ending the operation of the medical manipulator 1 will be described. The manipulator stopping procedure stops the operation of the medical manipulator 1 only when the joints of the medical manipulator 1 are set in their initial positional states (initial positions). The manipulator stopping procedure will be described with reference to FIG. 12. A control unit 40 that controls a power transmission mechanism 60 on the basis of instructions given by an operating unit 20 carries out the manipulator stopping procedure to set a part, connected to the second power transmission unit 63, of the first power transmission unit 61 at a predetermined initial position.

Thus, the operation of the medical manipulator 1 can normally be stopped only when the first power transmission unit 61 is set in its initial positional state (initial position). The first power transmission unit 61 can be restored to the initial positional state when the working unit 10 disconnected from the drive unit 50, cleaned and sterilized is connected again to the drive unit 50. Therefore, the medical manipulator 1 can be used immediately after the same has been connected to a power source without requiring any return-to-origin operation. Thus, troublesome work in a tense situation of surgical operation can be avoided and thereby the efficiency of the surgical operation can remarkably be improved.

In carrying out the following manipulator stopping procedure, the positional states of the joints are detected by incremental encoders combined with the joints and any origin sensors, such as absolute encoders, are not necessary.

Figure 12:
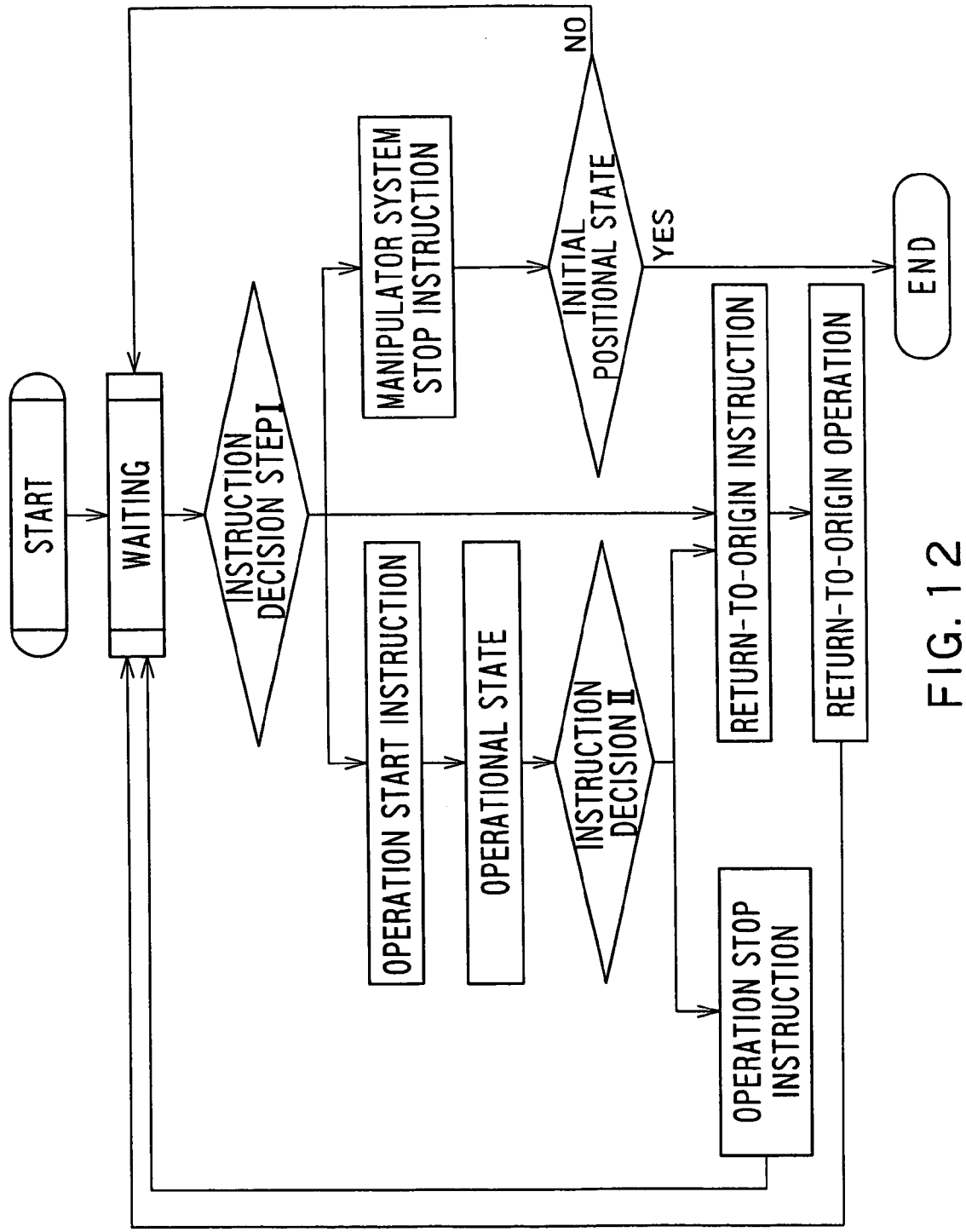
FIG. 12 is a flow chart of a procedure for operating the medical manipulator of the present invention.
Figure 13:
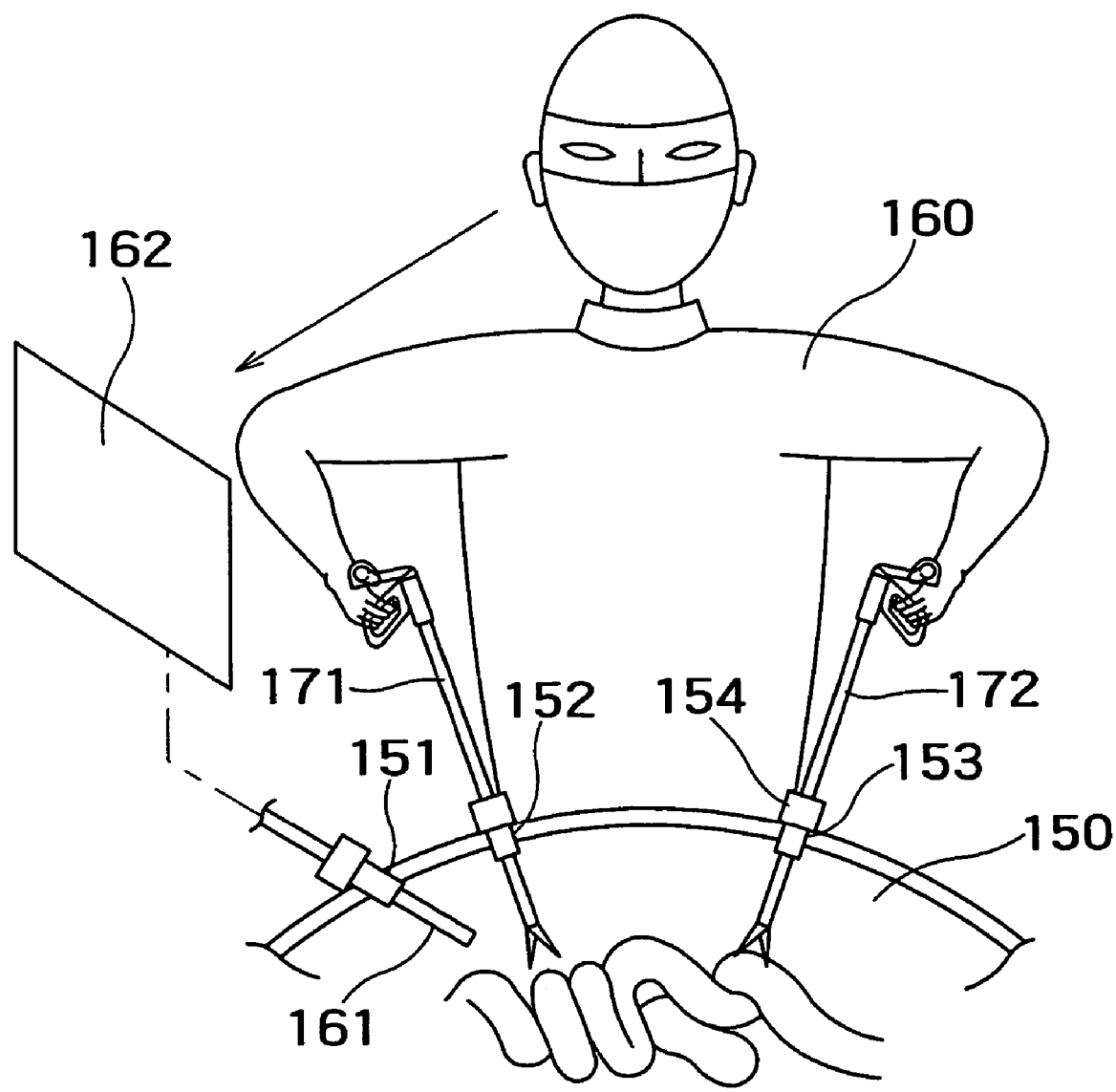
FIG. 13 is a pictorial view of assistance in explaining the use of a medical manipulator.
Figure 14:
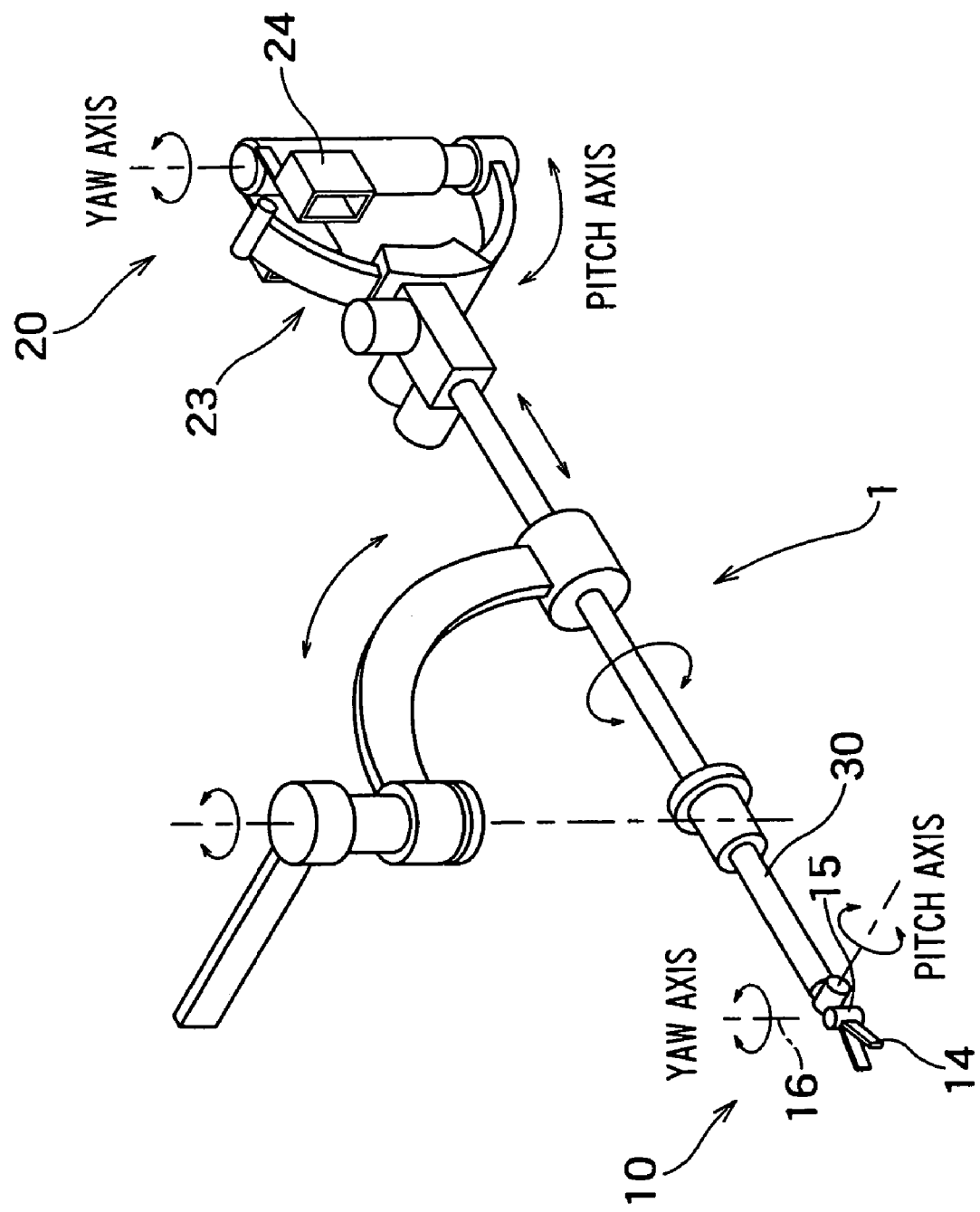
FIG. 14 is a perspective view of a conventional medical manipulator.
Figure 15:
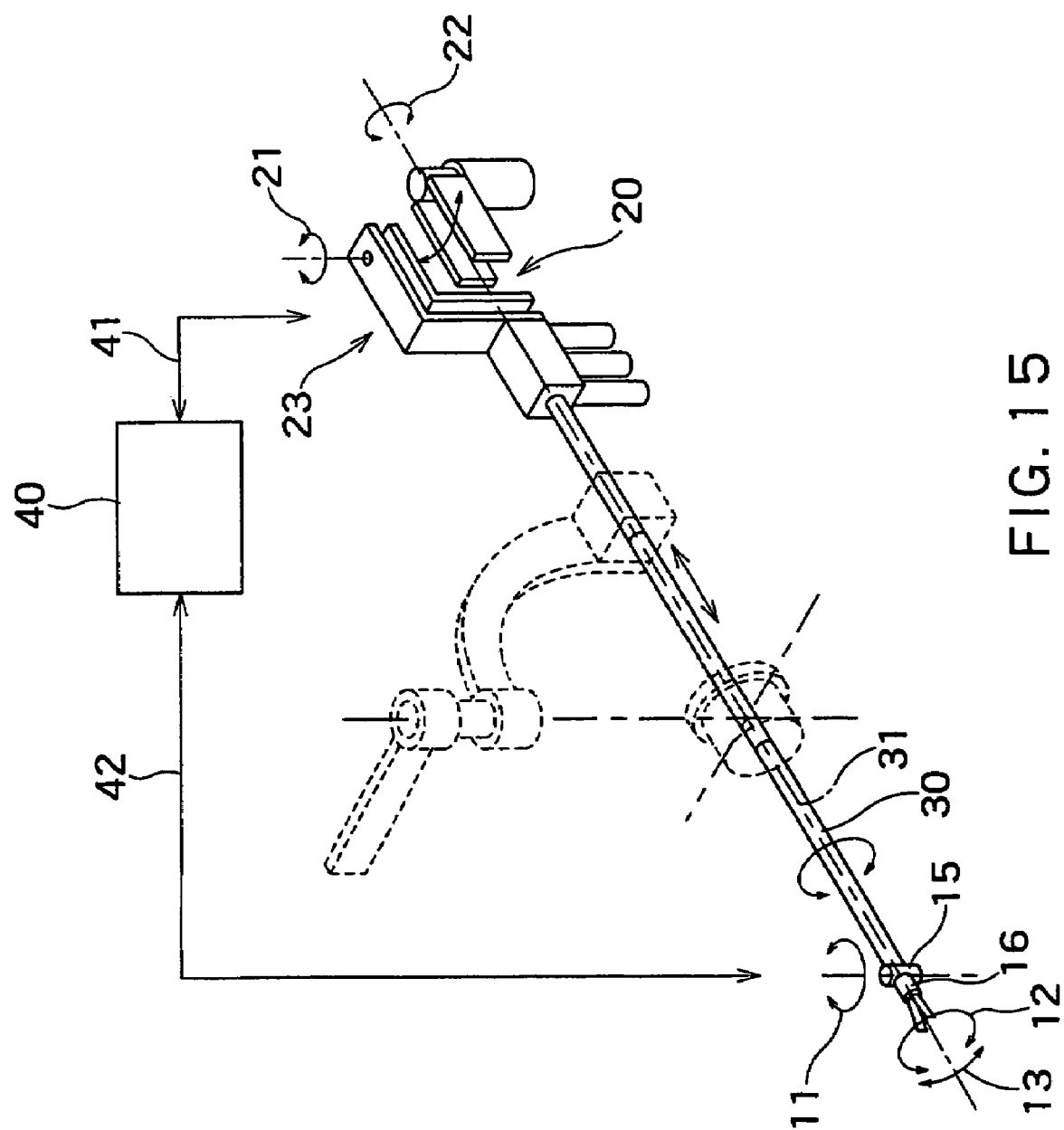
FIG. 15 is a perspective view of a conventional medical manipulator.

A manipulator system comprises the medical manipulator 1, and the control unit 40 for controlling the drive unit 50 of the medical manipulator 1. Referring to FIG. 12, the control unit 40 is initialized, a control program for controlling the medical manipulator 1 is started, and the medical manipulator 1 is set in a waiting state upon the connection of the manipulator system to a power source. When the manipulator system is set in the waiting state, the output shafts of the motors of the drive unit 50 are kept at the initial angular positions or current supply to the motors is inhibited, and the working unit 10 is held in an initial state. The controller 40 monitors instructions provided by the operating unit 20 periodically. The operator operates switches included in the control unit 40 and the operating unit 20, and foot switches and/or a keyboard connected to the manipulator system to provide instructions. The operator may give instructions by means of voice input means or pictorial means. A decision is made as to which one of an operation start instruction, a return-to-origin instruction and an operation stop instruction is given in an instruction decision step I, and the operating mode of the medical manipulator 1 is determined according to the instruction. The return-to-origin instruction and a return-to-origin operation are not those that controls an origin sensor to reset the origin sensor, but those that sets the joints in the initial positional states, respectively. In an operational state specified by the operation start instruction, the positional condition of the working unit 10 follows that of the operating unit 20. The operation stop instruction and the return-to-origin instruction are monitored, and the operating mode of the medical manipulator 1 is determined according to the instruction.

When the operation stop instruction is given, the medical manipulator 1 stops in a positional state in which the medical manipulator is set at the time when the operation stop instruction is given, and stays in a waiting state. The return-to-origin operation that is performed when the return-to-origin instruction is given operates the motors of the drive unit 50 so as to set the working unit 10 of the medical manipulator 1 in its initial positional state (initial position). After the working unit 10 has been set in the initial positional state, the medical manipulator 1 stays in the waiting state.

If it is decided that the operation stop instruction is given in the instruction decision step I, a query is made to see whether or not an operation ending operation is to be executed. The control unit 40 is capable of storing data on the variation of the operating mode of the medical manipulator 1 and is capable of deciding an operating state from which the medical manipulator 1 changed to the waiting state. If the medical manipulator 1 is in the return-to-origin operation immediately before the operating state changes into the waiting state, it is decided that the return-to-origin operation has been completed before the operation stop instruction is given, and an operation end operation is executed. If the medical manipulator 1 is in the operation end operation immediately before the state changes into the waiting state and the medical manipulator 1 is not in the return-to-origin operation, it is decided that the return-to-origin operation has not been completed before the operation stop instruction is given, and that the operation end operation is not executed.

Although the operation start instruction, the return-to-origin instruction and the operation stop instruction are used, the control unit 40 is capable of storing data on the variation of the operating mode of the medical manipulator 1 and is capable of deciding an operating state from which the medical manipulator 1 changed to the waiting state. Therefore, the operation of the manipulator system can be ended only when the medical manipulator 1 is in the initial positional state. The manipulator system may be controlled by any suitable control procedure other than hat shown in FIG. 12, provided that the control procedure is capable of ending the operation of the medical manipulator 1 normally.

When the manipulator system is thus constructed, the operator is able to recognize the abnormal state of the working unit 10 before starting the operation of the medical manipulator 1. If the working unit 10 is not in the initial positional state when the working unit 10 is interlocked with the drive unit 50, the operator is able to recognize such an abnormal condition of the working unit 10 easily. Possible causes that set the working unit 10 in a positional state other than the initial positional state are the abnormal end of the operation of the medical manipulator 1 due to emergency or such in the preceding surgical operation, and abnormal or incorrect connection of the power transmitting devices 64, 65 and 66 to the second power transmission unit 63 including faulty fastening of the wires, excessive elongation of the wires and such. A condition where the first power transmission unit 61 is not stopped in the initial positional state due to the emergency stop of the medical manipulator in the preceding surgical operation can be corrected. Therefore, basic causes of setting the working unit 10 in a positional state other than the initial positional state is the abnormal or incorrect connection of the power transmitting devices 64, 65 and 66 to the second power transmission unit 63. Thus, the operator is able to recognize the abnormal condition of the working unit 10 beforehand and, therefore, the medical manipulator 1 is safe.

Basically, it is impossible to restore the first power transmission unit 61 joined to the drive unit 50 to the initial positional state in interlocking the working unit 10 with the drive unit 50 when the medical manipulator 1 is stopped abnormally due to emergency during a surgical operation. However, in the medical manipulator 1 in the second embodiment of the present invention, the initialization detector 70 provided with an origin sensor can be detachably connected to the first power transmission unit 61 after the first power transmission unit 61 has been disconnected from the second power transmission unit 63. The initialization detector 70 is connected to the first power transmission unit 61, and the motors of the drive unit 50 are actuated to set the first power transmission unit 61 in its initial positional state. Since the first power transmission unit 61 can be set in the initial positional state beforehand, the troublesome return-to-origin operation does not need to be performed during a surgical operation. In a state where the initializing operation for setting the first power transmission unit 61 interlocked with the drive unit 50 in the initial positional state has been completed, the working unit 10 and the second power transmission unit 63 can be set in their initial positional states by connecting the second power transmission unit 63 interlocked with the working unit 10 to the first power transmission unit 61 interlocked with the drive unit 50. Thus, the medical manipulator 1 does not need any permanent, built-in origin sensor, can be formed in a small, lightweight structure and is excellent in operability.

If the medical manipulator 1 should be stopped for an emergency stop due to an emergency, the medical manipulator 1 must safely be retracted and removed from the subject without harming the subject. The medical manipulator 1 enables the disconnection of the first power transmission unit 61 interlocked with the drive unit 50 from the second power transmission unit 63 interlocked with the working unit 10 in a state where the working unit 10 is inserted in a part of the subject's body. It is possible that the working unit 10 harms the subject if the working unit 10 inserted in a part of the subject's body is moved inadvertently. The first power transmission unit 61 interlocked with the drive unit 50 can safely be disconnected from the second power transmission unit 63 with the working unit 10 held immovably. Since the drive unit 10 can easily be driven, the drive unit 10 can be set in a safe position by operating the unit drive 10 by, for example, another pair of forceps, if the working unit 10 is in a dangerous position. The drive unit 10 can be extracted through the tracheal tube even if the drive unit 10 is not restored to its reference position. If the surgical operation is interrupted when there is something wrong in the power transmitting devices, the components and structural members of the mechanism on the side of the working unit 10 and the mechanisms on the side of the drive unit 50 are perfectly controllable, the manipulator system can simply and quickly be set to rights without requiring troublesome operations for initializing and starting the manipulator system at all simply by replacing the defective working unit 10 with a new one and connecting the second power transmission unit 63 interlocked with the working unit 10 to the first power transmission unit 61 interlocked with the drive unit 50. If the initial positional state of the drive unit 50 is not preserved due to the abnormal end of the operation of the medical manipulator 1, the drive unit 50 can be restored to its initial positional state by using the initialization detector 70.

As apparent from the foregoing description, according to the present invention, the working unit can be cleaned and sterilized, a return-to-origin operation can be carried out without using any absolute encoders or origin sensors, and the working unit can always be set in its initial state before and after connecting the working unit to and disconnecting the same from the drive unit, the medical manipulator can be formed in a small, lightweight structure, and has an improved operability because the first power transmission unit and the second power transmission unit can detachably be connected, and the first power transmission unit is capable of exerting a back drive torque sufficient for locating the second power transmission unit such that the first and the second power transmission unit are connected in the same positional relationship as a predetermined positional relationship in which the first and the second power transmission unit had been connected before the same were separated from each other.

Since the control unit sets the first power transmission unit in the predetermined initial positional state after the normal completion of an operation, the medical manipulator can necessarily be restored to the initial positional state when the work unit is interlocked again with the drive unit after disengaging the work unit from the drive unit, cleaning and sterilizing the work unit after the completion of a surgical operation. Thus, the medical manipulator can be used immediately after the connection of the same to the power source without requiring a troublesome return-to-origin operation. Thus, troublesome work in a tense situation of surgical operation can be avoided and thereby the efficiency of the surgical operation can remarkably be improved.

Since the initialization detecting means is capable of being detachably connected to the first power transmission unit, the initialization of the drive unit can be detected without permanently mounting the initialization detecting means on the first power transmission unit, and the returnto-origin operation is possible even in a state where the operation is ended abnormally. Since the medical manipulator does not need to be provided with any origin sensor, the medical manipulator can be formed in a small, lightweight structure and has an improved operability. Furthermore, the medical manipulator is safe because the initialization detector can easily be connected to and disconnected from the first power transmission unit even in an emergency during a surgical operation without causing harm to the subject.

Although the invention has been described in its preferred embodiment with a certain degree of particularity, obviously many changes and variations are possible therein. It is therefore to be understood that the present invention may be practiced otherwise than as specifically described herein without departing from the scope and spirit thereof.

What is claimed is:

1. A medical manipulator comprising:
    a working unit that performs operations;
    an operating unit that generates instructions;
    a drive unit that drives the working unit on the basis of instructions given thereto by the operating unit;
    a power transmission mechanism for transmitting driving force of the drive unit to the working unit; and
    a control unit for controlling the power transmission mechanism on the basis of instructions given thereto by the operating unit;
    wherein the power transmission mechanism includes a first power transmission unit interlocked with the drive unit, and a second power transmission unit interlocked with the working unit and capable of being detachably connected to the first power transmission unit.

2. The medical manipulator according to claim 1, wherein the control unit is capable of executing operations specified by a control program for setting the first power transmission unit in a predetermined initial positional state at the normal completion of an operation.

3. The medical manipulator according to claim 2, wherein the control program waits in a waiting state where the control unit is initialized by connecting the medical manipulator to a power source for an operation start instruction specifying an operation for setting the operating unit in an operational state, a return-to-origin instruction specifying an operation for setting the first power transmission unit in the predetermined initial positional state or a shutdown instruction specifying an operation for disconnecting the medical manipulator from the power source, and the control program makes the shutdown instruction effective only when it is confirmed that the first power transmission unit has been set in the predetermined initial positional state.

4. The medical manipulator according to claim 1 further comprising an initialization detecting means capable of being connected to the first power transmission unit when the first power transmission unit is disconnected from the second power transmission unit and of detecting components of the first power transmission unit set at predetermined joining positions, respectively.

5. The medical manipulator according to claim 1, wherein the working unit and the second power transmission unit are integrated in an assembly, the operating unit and the first power transmission unit are integrated in an assembly, and the assembly of the working unit and the second power transmission unit, and the assembly of the operating unit and the first power transmission unit can detachably connected together.

6. The medical manipulator according to claim 1, wherein the working unit and the second power transmission unit are integrated in an assembly; and the assembly of the working unit and the second power transmission unit, the first power transmission unit, and the operating unit can detachably be connected together.

* * * * *